(12) United States Patent
Kim

(10) Patent No.: US 11,612,735 B1
(45) Date of Patent: Mar. 28, 2023

(54) SMART SAFETY REGULATION SYSTEM OF RINGER SOLUTION

(71) Applicant: Jason Kim, Seoul (KR)

(72) Inventor: Jason Kim, Seoul (KR)

( * ) Notice: Subject to any disclaimer, the term of this patent is extended or adjusted under 35 U.S.C. 154(b) by 0 days.

(21) Appl. No.: 17/987,106

(22) Filed: Nov. 15, 2022

(30) Foreign Application Priority Data

Sep. 23, 2022 (KR) ........................ 10-2022-0120959

(51) Int. Cl.
*A61M 39/28* (2006.01)
*A61M 5/168* (2006.01)

(52) U.S. Cl.
CPC ........ *A61M 39/28* (2013.01); *A61M 5/16813* (2013.01); *A61M 5/16877* (2013.01)

(58) Field of Classification Search
CPC .. A61M 39/28; A61M 39/283; A61M 39/285; A61M 39/286; A61M 39/287; A61M 5/002; A61M 5/168; A61M 5/16804; A61M 5/16813; A61M 5/16877; A61M 5/16881
See application file for complete search history.

(56) References Cited

U.S. PATENT DOCUMENTS

| 2,245,030 | A | * | 6/1941 | Gottesfeld | ............ | A61M 39/28 |
| | | | | | | 606/209 |
| 2009/0043253 | A1 | * | 2/2009 | Podaima | ................ | G16H 10/60 |
| | | | | | | 604/67 |

FOREIGN PATENT DOCUMENTS

| CN | 2905083 | Y | * | 5/2007 |
| CN | 102886088 | B | * | 2/2014 |
| JP | 2006102279 | A | * | 4/2006 |
| KR | 10-0664615 | B1 | | 1/2007 |
| KR | 20-0474401 | Y1 | | 9/2014 |
| KR | 10-1481918 | B1 | | 1/2015 |
| KR | 10-2171665 | B1 | | 10/2020 |
| KR | 10-2411065 | B1 | | 6/2022 |

* cited by examiner

*Primary Examiner* — Shefali D Patel
(74) *Attorney, Agent, or Firm* — KORUS Patent, LLC; Seong Il Jeong

(57) ABSTRACT

Provided is a smart safety regulation system of Ringer solution, which includes: a regulator body having a body frame; a lower roller rotatably disposed inside the body frame; a flow regulating roller rotatably disposed inside the body frame and apart from an upper surface of the lower roller wherein a portion of an outer periphery of the flow regulating roller protrudes through an open upper side of the body frame; and a safety cover which accommodates the regulator body detachably. The system has an effect that a flow of the Ringer solution will not change even if a patient misoperates or does not operate skillfully in order to prevent medical accidents.

3 Claims, 5 Drawing Sheets

SMART SAFETY REGULATION SYSTEM OF RINGER SOLUTION

TECHNICAL FIELD

The present disclosure relates to a smart safety regulation system of Ringer solution.

BACKGROUND ART

An existing automatic regulation device of Ringer solution flow for intravenous injection is disclosed in the Korea patent publication No. 10-2005-0014908 (publication date: Feb. 7, 2005). According to the disclosure, patients or guardians can confirm the injection status of intravenous injection at any time, and can also solve the inconvenience problem of directly adjusting the injection speed according to the needs, but on the other hand, there is a fundamental problem of complex structure.

Furthermore, an existing regulation device of Ringer solution flow is disclosed in the Korea utility model publication No. 20-0474401 (registration date: Sep. 3, 2014). According to the disclosure, user can move the roller shaft to right and left one grid at a time to adjust the amount of the Ringer solution dropped, so that the user can check how much solution is put into the blood by observing the position of the roller shaft, but as there is no safety device, this may be cause medical accident due to the non-skilled operation of the non-medical personnel.

DISCLOSURE OF THE INVENTION

Technical Problem

To solve the above problem, an object of the present invention is to provide a smart safety regulation system of Ringer solution, which can prevent medical accidents caused by the operations of patients and other non-medical personnel.

Technical Solution

The object of the invention may be realized by the following smart safety regulation system of Ringer solution. The A smart safety regulation system of Ringer solution, comprising: a regulator body includes a body frame has a hollow structure with open the front side, the back side and the top side; a lower roller rotatably disposed inside the body frame; a flow regulating roller rotatably disposed inside the body frame and apart from the upper surface of the lower roller, and a portion of the outer peripheral of the flow regulating roller protrude through the opened upper side of the body frame; and a safety cover has a hollow structure with open the front side, the back side and the bottom side and accommodates the regulator body detachably, the regulator body further comprises a guide through hole formed on the two sides of the body frame, the regulator body further comprises a locking bolt that passed through the guide through hole to connected with the flow regulating roller, the locking bolt comprises a connecting end and a connecting head, the connecting end is the one end of the locking bolt that passed through the guide through hole and connected with the rotating center of the flow regulating roller, the connecting head is integrated with the other end of the connecting end and connected to between first position and second position, the first position is a position that the connecting head fit to the body frame to restrains the flow regulating roller, and the second position is a position that the connecting head separated from the body frame and make the flow regulating roller rotatable.

Preferably, the regulator body further comprises a safety cover fixing groove formed on the two side of the body frame, the safety cover further includes a cover body, having a blocking piece disposed lower end of the inner side of the cover body and detachable on the safety cover fixing groove; a observation window provided on the upper side of the cover body; and a plurality of non-slip bulges formed on the two sides of the safety cover, the regulator body further comprises a safety cover anti-off bolt connecting the safety cover and the regulator body.

Preferably, the present disclosure further comprises a tube supporting component provided on the safety cover, the tube supporting component includes: a fixing bulge provided on the front upper end of the safety cover; a elastic connecting belt connected with the fixing bulge at one end; and a tube supporting pipe body, the other end of the elastic connecting belt is connected to the outer peripheral of the tube supporting pipe body.

Advantageous Effects

The present disclosure as mentioned above has an effect that the flow of the Ranger's solution will not change even if the patient misoperates or does not operate skillfully, so that can prevent medical accidents. Furthermore, the present disclosure has the advantage that can prevent medical accidents caused by the operation of the non-medical personnel.

DETAILED DESCRIPTION

Figure 1:
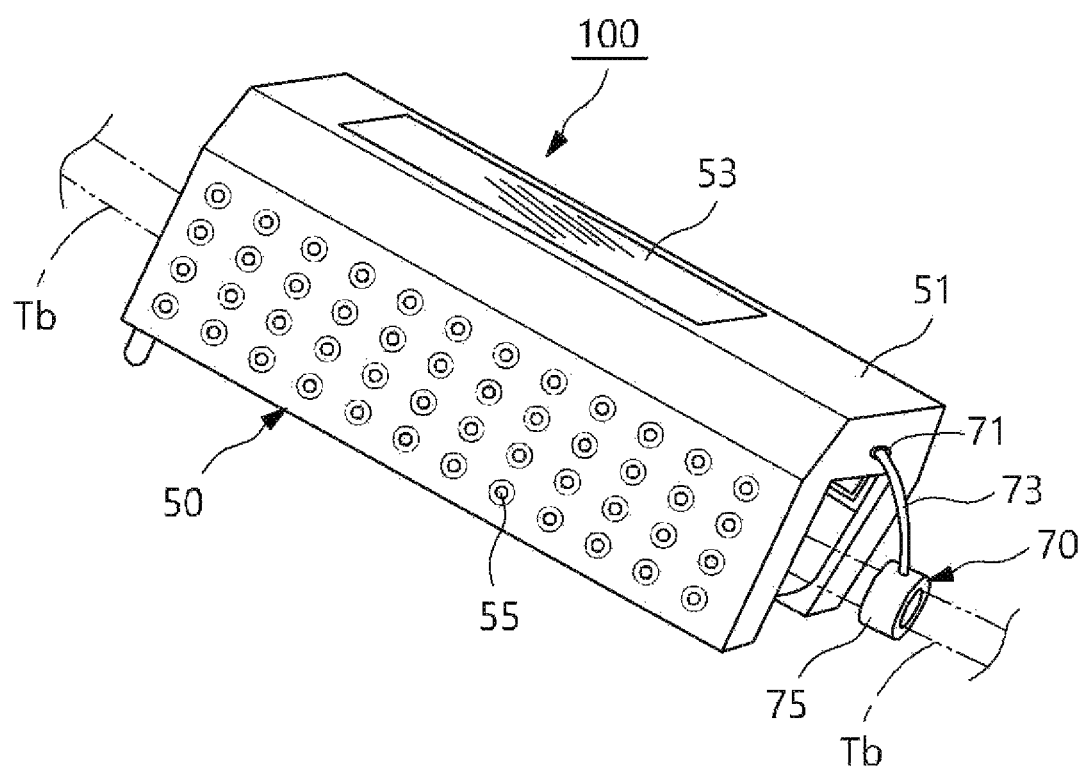
FIG. 1 is an oblique view of smart safety regulation system of Ringer solution according to the present invention.
Figure 2:
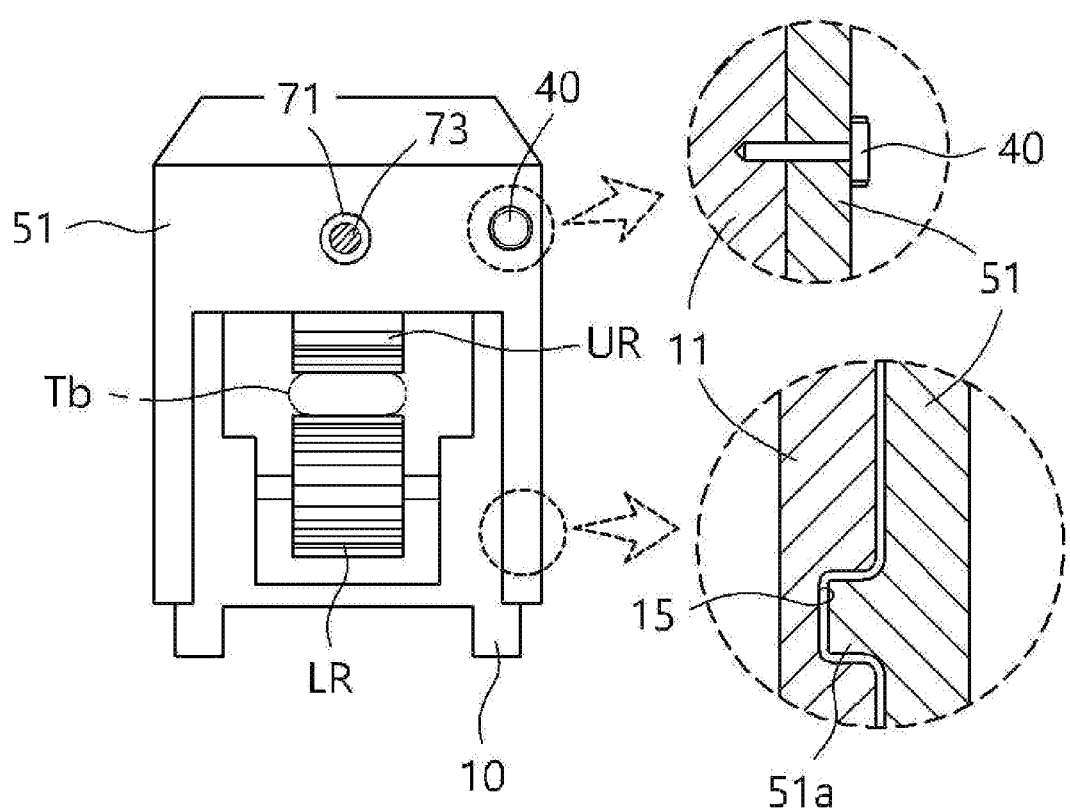
FIG. 2 is a side view of FIG. 1.

Hereinafter, a embodiment of the present invention will be described with reference to the accompanying drawings.

The smart safety regulation system of Ringer solution 100 according to the present invention comprises a regulator body 10, a safety cover 50, a plurality of safety cover anti-off bolts 40, a lower roller LR, a locking bolt 60, a flow regulating roller UR and a tube supporting component 70, as shown in FIGS. 1-4B.

The Regulator body 10 includes a body frame 11, a guide through hole 13 and a safety cover fixing groove 15. The body frame 11 has a hollow structure with open the front side, the back side and the top side. The guide through hole 13 formed on the two sides of the body frame 11 (only one end is shown in the figure). The safety cover fixing groove 15 is formed on the two sides of body frame 11 (only one end is shown in the figure). Herein, the Regulator body 10 is a well-known component other than the guide through hole 13 and the safety cover fixing groove 15, therefore, the description or illustration of it will be omitted.

The lower roller LR is rotatably located inside the body frame 11. Wherein, the lower roller LR may be set to one or more.

The flow regulating roller UR is located apart from the upper surface of the lower roller LR and rotatably disposed inside the body frame 11, and a portion of the outer peripheral surface of the flow regulating roller UR protrudes through the opened upper side of the body frame 11. The flow regulating roller UR can move forward and backward along the guide through hole 13. Herein, a portion of the outer peripheral surface of the flow regulating roller UR is exposed through the opened upper side of the body frame 11, so that the user can rotates the peripheral of the flow regulating roller UR to compress or decompress the intravenous injection tube Tb to regulate the flow of the Ringer solution.

Figure 3:
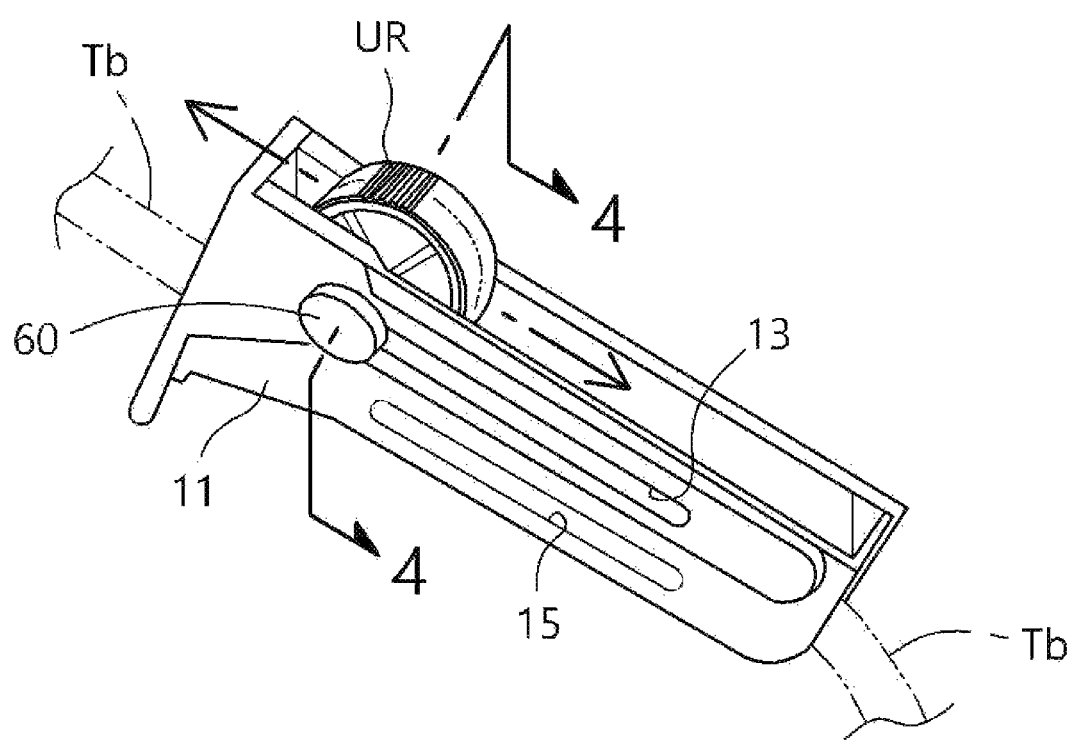
FIG. 3 is an oblique view showing the state of removing the safety cover shown in FIG. 1.
Figure 4A:
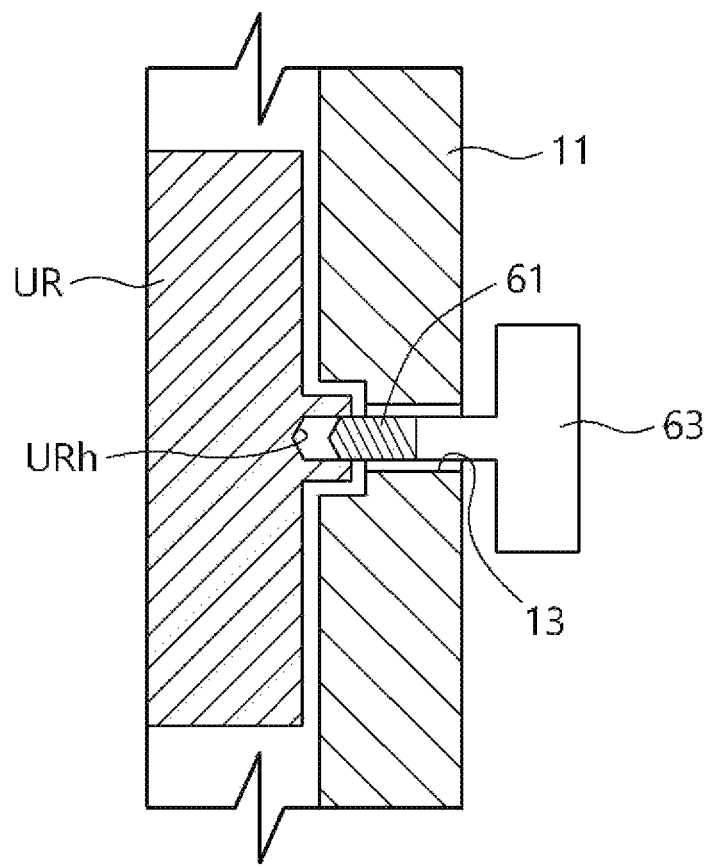
FIGS. 4A and 4B are sectional views showing the connection relationship between the locking bolt and the flow regulating roller.
Figure 4B:
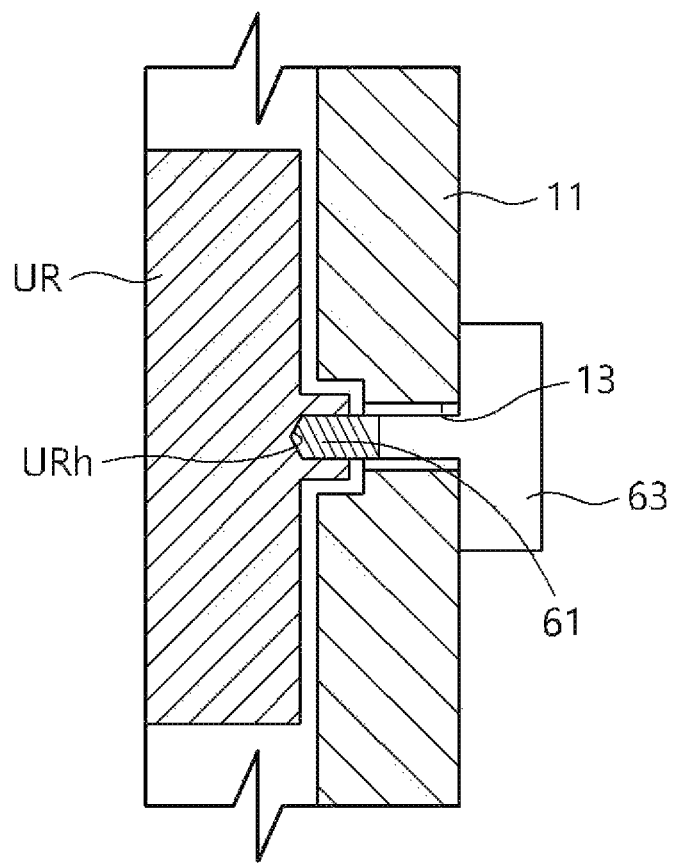

The intravenous injection tube Tb is located between the outer peripheral of the lower roller LR and the outer peripheral of the flow regulating roller UR, and when the flow regulating roller UR moves forward as shown in FIG. 3, the flow regulating roller UR will be closer to the outer peripheral of the lower roller LR and then compress the intravenous injection tube Tb, if it is contrary to this, if the flow regulating roller UR moves backward, the flow regulating roller UR will away from the outer peripheral of the lower roller LR and then decompress the intravenous injection tube Tb.

The safety cover 50 includes a cover body 51 and a observation window 53. The cover body 51 has a hollow structure with open the front side, the back side and the bottom side, and accommodates the regulator body 10 in a detachable way. The observation window 53 is provided on the upper side of the cover body 51. The non-slip bulges 55 is further disposed at the two sides of the safety cover 50 (only one side is shown in the figure). The cover body 51 is provided with a blocking piece 51a on the lower end of its inner side, and the blocking piece 51a is inserted into the safety cover fixing groove 15. The user can inserts the blocking piece 51a in the safety cover fixing groove 15 to accommodates the regulator body 10, on the contrary, the user can separates the lower end of the cover body 51 to disassemble and remove the blocking piece 51a from the safety cover fixing groove 15. Herein, it should be understandable that the connection relationship of the safety cover 50 and the regulator body 10 is merely an example, and it can deform into various ways.

The observation window 53 is used for the user to visually confirm the internal state, and it made of transparent acrylic, glass, etc.

The safety cover anti-off bolts 40 can connect the cover body 51 and the body frame 11, so that prevent the safety cover 50 from falling off due to the user's carelessness.

The locking bolt 60 includes a connecting end 61 passed through the guide through hole 13 and a connecting head 63. The connecting end 61 is joined with the rotating center URh of the flow regulating roller UR. The connecting head 63 is integrated with the other end of the connecting end 61 and connected to between first position and second position. The first position is a position that the connecting head 63 fit to the body frame 11 to restrains the flow regulating roller UR, and the second position is a position that the connecting head 63 separated from the body frame 11 and make the flow regulating roller UR rotatable. Herein, according to the connection mode, the locking bolt 60 can use a method that make the flow regulating roller UR can rotate or be restrained, but it is merely an example.

The tube supporting component 70 includes a fixing bulge 71 provided on the front upper end of the safety cover 50, an elastic connecting belt 73 which one end is connected with the fixing bulge 71, and a tube supporting pipe body 75. Another end of the elastic connecting belt 73 is connected on the outer peripheral of the tube supporting pipe body 75. Herein, the tube supporting component 70 is provided in order to safely supporting the intravenous injection tube Tb located at outer side of the safety cover 50 so that the intravenous injection tube Tb will not sag or shake, therefore, the inner diameter of the tube supporting pipe body 75 is greater than the outer diameter of the intravenous injection tube Tb, and the elastic connecting belt 73 is made of rubber band or wire.

The present discloser is described with the above one embodiment, but it is not intended to limit the protect scope of the present application, and the whole embodiments that basis on the spirit of the present application are all in the scope of the present application.

DESCRIPTION OF SYMBOLS

10: regulator body
40: safety cover anti-off bolt
50: safety cover
60: locking bolt
LR: lower roller
UR: flow regulating roller
100: smart safety regulation system of Ringer solution

What is claimed is:

1. A smart safety regulation system of Ringer solution, comprising:
    a regulator body including a body frame having a hollow structure with a front side, a back side and a top side being open;
    a lower roller rotatably disposed inside the body frame;
    a flow regulating roller rotatably disposed inside the body frame and apart from an upper surface of the lower roller wherein a portion of an outer periphery of the flow regulating roller protrudes through the open top side of the body frame; and
    a safety cover having a hollow structure with a front side, a back side and a bottom side being open and accommodating the regulator body detachably,
    the regulator body further comprising a guide through hole formed on two sides of the body frame,
    the regulator body further comprising a locking bolt that passes through the guide through hole to connect with the flow regulating roller,
    the locking bolt comprising a connecting end and a connecting head,
    the connecting end is one end of the locking bolt that passes through the guide through hole and connects with a rotating center of the flow regulating roller,
    the connecting head is integrated with the connecting end at other end of the locking bolt and moves between a first position and a second position, the first position is a position that the connecting head fits to the body frame to restrain the flow regulating roller, and the second position is a position that the connecting head separates from the body frame and makes the flow regulating roller rotatable.

2. The smart safety regulation system of Ringer solution of claim 1, wherein the regulator body further comprises a safety cover fixing groove formed on the two sides of the body frame,
    the safety cover further including a cover body having a blocking piece disposed on a lower end of an inner side of the cover body and detachable on the safety cover fixing groove; an observation window provided on an upper side of the cover body; and a plurality of non-slip bulges formed on two sides of the safety cover, the regulator body further comprising a safety cover anti-off bolt connecting the safety cover and the regulator body.

3. The smart safety regulation system of Ringer solution of claim 1, further comprising a tube supporting component provided on the safety cover, the tube supporting component including a fixing bulge provided on a front upper end of the safety cover; an elastic connecting belt connected with the fixing bulge at one end of the elastic connecting belt; and a tube supporting pipe body, other end of the elastic connecting belt is connected to an outer periphery of the tube supporting pipe body.

* * * * *